United States Patent
Kozerski et al.

(10) Patent No.: US 9,682,992 B2
(45) Date of Patent: Jun. 20, 2017

(54) DERIVATIVES OF CAMPTOTHECIN, A METHOD OF PRODUCING THEM AND THEIR USE

(71) Applicants: INSTYTUT CHEMII ORGANICZNEJ POLSKIEJ AKADEMII NAUK, Warsaw (PL); NARODOWY INSTYTUT LEKÓW, Warsaw (PL)

(72) Inventors: Lech Kozerski, Warsaw (PL); Robert Kawęcki, Warsaw (PL); Beata Naumczuk, Bielsk Podlaski (PL); Karolina Hyz, Warsaw (PL); Wojciech Bocian, Warsaw (PL); Jerzy Sitkowski, Warsaw (PL); Elżbieta Bednarek, Warsaw (PL); Katarzyna Wiktorska, Warsaw (PL); Katarzyna Lubelska, Warsaw (PL)

(73) Assignees: INSTYTUT CHEMII ORGANICZNEJ POLSKIEJ AKADE, Warsaw (PL); NARODOWY INSTYTUT LEKÓW, Warsaw (PL)

( * ) Notice: Subject to any disclaimer, the term of this patent is extended or adjusted under 35 U.S.C. 154(b) by 0 days.

(21) Appl. No.: 14/432,553

(22) PCT Filed: Oct. 25, 2013

(86) PCT No.: PCT/IB2013/059668
§ 371 (c)(1),
(2) Date: Mar. 31, 2015

(87) PCT Pub. No.: WO2014/064654
PCT Pub. Date: May 1, 2014

(65) Prior Publication Data
US 2015/0266888 A1    Sep. 24, 2015

(30) Foreign Application Priority Data

Oct. 25, 2012   (PL) .......................... 401345

(51) Int. Cl.
| C07D 221/18 | (2006.01) |
| C07D 221/22 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| A61K 31/44 | (2006.01) |
| C07D 491/22 | (2006.01) |

(52) U.S. Cl.
CPC .................................. *C07D 491/22* (2013.01)

(58) Field of Classification Search
None
See application file for complete search history.

(56) References Cited

U.S. PATENT DOCUMENTS 5,004,758 A * 4/1991 Boehm ................ C07D 491/22
514/233.2

FOREIGN PATENT DOCUMENTS

| CN | 101133813 | 5/2013 |
| JP | 03232888 | 10/1991 |
| JP | 03232888 A * | 10/1991 |
| WO | 2008012003 | 1/2008 |
| WO | 2011154574 | 12/2011 |

OTHER PUBLICATIONS

Freshney, RI. Culture of Animal Cells: A Manual of Basic Technique. John Wiley and Sons. 2005, 5th Ed., p. 8.*
National Research Council (US) Steering Committee on Identification of Toxic and Potentially Toxic Chemicals for Consideration by the National Toxicology Program. Toxicity Testing: Strategies to Determine Needs and Priorities. Washington (DC): National Academies Press (US); 1984, p. 1.*
Kunimoto, T. et al. Antitumor Activity of 7-Ethyl-10-[4-(1-piperidino)-1-piperidino]carbonyloxy-camptothecin, a Novel Water-soluble Derivative of Camptothecin, against Murine Tumors. Cancer Research. 1987, vol. 47, p. 5945.*
Kingsbury, W.D. et al., "Syntehsis of Water-Soluble (Aminoalkyl) camptothecin Analogues: Inhibition of Topoisomerase I and Antitumor Activity", American Chemical Society US, vol. 34, No. 1, 1991, pp. 98-107.
International Search Report issued by the International Searching Authority (ISA/O.E.P.M.) on Mar. 11, 2014 in connection with International Application No. PCT/IB2013/059668.
Swada, Seigo et al., "Preparation of anticancer water-soluble camptothecins", retrieved from STN Database accession No. 1992:83994 abstract.

* cited by examiner

Primary Examiner — Noble Jarrell
Assistant Examiner — Ben S Michelson
(74) Attorney, Agent, or Firm — Gary J. Gershik; Cooper & Dunham LLP

(57) ABSTRACT

The subject of the present invention are water-soluble derivatives of camptothecin, their synthesis and use. These compounds exhibit preferable biological properties for use in anti-neoplasm therapy.

11 Claims, 5 Drawing Sheets

DERIVATIVES OF CAMPTOTHECIN, A METHOD OF PRODUCING THEM AND THEIR USE

This application is a §371 national stage of PCT International Application No. PCT/IB2013/059668, filed Oct. 25, 2013, designating the United States and claiming priority of Polish Application No. PL401345, filed Oct. 25, 2012, the contents of all of which are hereby incorporated by reference into this application.

The subject of the present invention are water-soluble derivatives of camptothecin, their synthesis and use. These compounds exhibit preferable biological properties, useful in anti-neoplasm therapy.

Topoisomerases are important enzymes that convert the chemical energy of molecules with a superhelical structure. These enzymes unwind the DNA double helix weakening the twisting tension of the DNA molecule, making the template accessible to replication or transcription enzymes[1,2].

In the case of topoisomerase I (topo I), responsible for the degradation of one bond through nicking one strand and the relaxation of supercoiled DNA, in humans this reaction occurs with the participation of Tyr723, which interacts with the phosphate skeleton causing the formation of 3'-phosphotyrosine.[3] As a result of the rotation of the nicked strand, the DNA interacts with the released 5'-OH group of phosphotyrosine.[2] In this way, various small aromatic molecules, such as camptothecin (CPT), a naturally occurring product, or its derivative topotecan (TPT), known in clinical use as Hycamtin™,[4,5,6] may be incorporated into the degradation site caused by topo I activity and stabilize the DNA-topo I complex.[7-10] This leads to cell death, which explains why TPT and its analogues are usually classified as poisons that change the significant enzyme into a DNA-damaging molecule. Topoisomerase I and II "poisons" are objects of great interest in biochemistry, because they constitute an important chemotherapeutic method of combating cancer.

The inhibition of topoisomerase I DNA is thus an important method of fighting cancer using chemotherapy. There are a number of effective bioorganic strategies of use in achieving this goal, such as the non-covalent binding of the poison at the site of degradation,[8,11,12] crosslinking using binding metals,[13] DNA alkylation[14,15] or photochemical DNA damage.[16]

Derivatives belonging to the camptothecin family play a significant role, such as Hycamtin™ or irinotecan, or Camptosar™, are used in clinical treatment as anti-cancer agents. So far, all known derivatives that participate in the inhibition of topo I merely form complexes with the nicked DNA. In conjunction with the abovementioned molecular complex structure, these compounds poorly bind tumour DNA.

There is little data regarding the photochemical transformation using compounds of the camptothecin family (CPT). There is also a lack of other possible mechanisms of the interaction of camptothecin derivatives with tumour DNA. Extant publications concentrate only on the inhibition of the enzyme topo I by way of forming tripartite complexes containing an oligomer of DNA/topo I/organic ligand.

There is thus a large need to deliver a new solution, ensuring the formation of a stable complex using camptothecin derivatives.

The present invention relates to the synthesis of novel, water-soluble derivatives exhibiting unexpected preferable properties in terms of covalent DNA binding.

The subject of the present invention is a compound defined by the general formula (I):

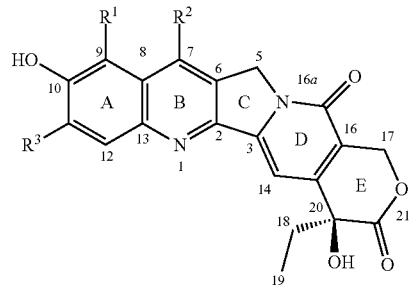

where $R^1$ denotes (N-piperidinyl)methyl; (N-piperazinyl)methyl; (N—(N-methylpiperazinyl)methyl; (N-morpholinyl)methyl; (N-pirolidynyl)methyl; (N-azetidinyl)methyl; (N-aziridinyl)methyl; (N-methylamino)methyl; (N,N-diethylamino)methyl; $R^2$ denotes ethyl; $R^3$ denotes H; (N-piperidinyl)methyl; (N-piperazinyl)methyl; (N—(N-methylpiperazinyl)methyl; (N-morpholinyl)methyl; (N-pirolidynyl)methyl; (N-azetidinyl)methyl; (N-aziridinyl)methyl; (N-methylamino)methyl; (N,N-diethylamino)methyl;

or $R^1$ denotes H; $R^2$ denotes ethyl; $R^3$ denotes (N-piperidinyl)methyl; (N-piperazinyl)methyl; (N—(N-methylpiperazinyl)methyl; (N-morpholinyl)methyl; (N-pirolidynyl)methyl; (N-azetidinyl)methyl; (N-aziridinyl)methyl; (N-methylamino)methyl; (N,N-diethylamino)methyl.

A compound according to the present invention is preferably a compound selected from a group encompassing:
7-ethyl-9-(N-morpholinyl)methyl-10-hydroxycamptothecin,
7-ethyl-11-(N-morpholinyl)methyl-10-hydroxycamptothecin,
7-ethyl-9,11-bis(N-morpholinyl)methyl-10-hydroxycamptothecin,
7-ethyl-9-(N-piperidinyl)methyl-10-hydroxycamptothecin,
7-ethyl-11-(N-piperidinyl)methyl-10-hydroxycamptothecin,
7-ethyl-9,11-bis(N-piperidinyl)methyl-10-hydroxycamptothecin,
7-ethyl-9-(N-piperazinyl)methyl-10-hydroxycamptothecin,
7-ethyl-11-(N-piperazinyl)methyl-10-hydroxycamptothecin,
7-ethyl-9,11-bis(N-piperazinyl)methyl-10-hydroxycamptothecin,
7-ethyl-9-(N—(N-methylpiperazinyl)methyl-10-hydroxycamptothecin,
7-ethyl-11-(N—(N-methylpiperazinyl)methyl-10-hydroxycamptothecin,
7-ethyl-9,11-bis(N—(N-methylpiperazinyl)methyl-10-hydroxycamptothecin,
7-ethyl-9-(N-pirolidynyl)methyl-10-hydroxycamptothecin,
7-ethyl-11-(N-pirolidynyl)methyl-10-hydroxycamptothecin,
7-ethyl-9,11-bis(N-pirolidynyl)methyl-10-hydroxycamptothecin,
7-ethyl-9-(N-azetidinyl)methyl-10-hydroxycamptothecin,
7-ethyl-11-(N-azetidinyl)methyl-10-hydroxycamptothecin, 7-ethyl-9,11-bis(N-azetidinyl)methyl-10-hydroxycamptothecin,
7-ethyl-9-(N-aziridinyl)methyl-10-hydroxycamptothecin,
7-ethyl-11-(N-aziridinyl)methyl-10-hydroxycamptothecin,
7-ethyl-9,11-bis(N-aziridinyl)methyl-10-hydroxycamptothecin,
7-ethyl-9-(N-methylamino)methyl-10-hydroxycamptothecin,
7-ethyl-11-(N-methylamino)methyl-10-hydroxycamptothecin,
7-ethyl-9,11-bis(N-methylamino)methyl-10-hydroxycamptothecin,
7-ethyl-9-(N,N-diethylamino)methyl-10-hydroxycamptothecin,
7-ethyl-11-(N,N-diethylamino)methyl-10-hydroxycamptothecin,
7-ethyl-9,11-bis(N,N-diethylamino)methyl-10-hydroxycamptothecin.

Another subject of the present invention is a method of obtaining the above-defined compounds, characterised in that compound SN38, 7-ethyl-10-hydroxycamptothecin, is subjected to a reaction with an appropriate amine and formaldehyde in an environment of acetonitrile and acetic acid at boiling temperature and this results in derivatives of 10-hydroxycamptothecin substituted as in the definition of compounds defined by the formula (I).

The next subject of the present invention is an intermediate compound (QM) o-methylenequinone defined by the formula (II) appropriate for substituting compounds defined by the formula (I) as defined above:

(II)

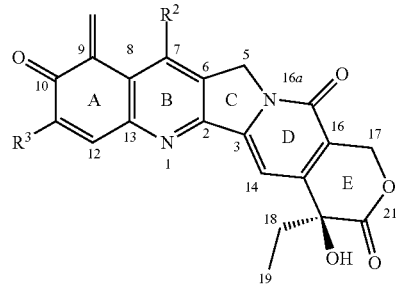

(III)

The subject of the present invention is also the use of the intermediate compound defined by the formula (II) in the production of anti-neoplasm drugs.

Preferably, this compound is useful in the production of a drug for the treatment of breast cancer.

Preferably, this compound is useful in the production of a drug for the treatment of leukaemia.

Preferably, this compound is useful in the production of a drug for the treatment of colon cancer.

The subject of the present invention is also the use of the intermediate compound defined by the formula (III) in the production of anti-neoplasm drugs.

Preferably, this compound is useful in the production of a drug for the treatment of breast cancer.

Preferably, this compound is useful in the production of a drug for the treatment of leukaemia.

Preferably, this compound is useful in the production of a drug for the treatment of colon cancer.

According to the present invention, ring A of TPT may undergo a photochemically-induced transformation into the intermediate compound o-methylenequinone, which may react in situ with the nucleophilic centres of guanine in duplex DNA (Schematic 1).

Moreover, compounds according to the present invention exhibit the property of spontaneous, covalent binding of DNA oligomers.

Schematic 1

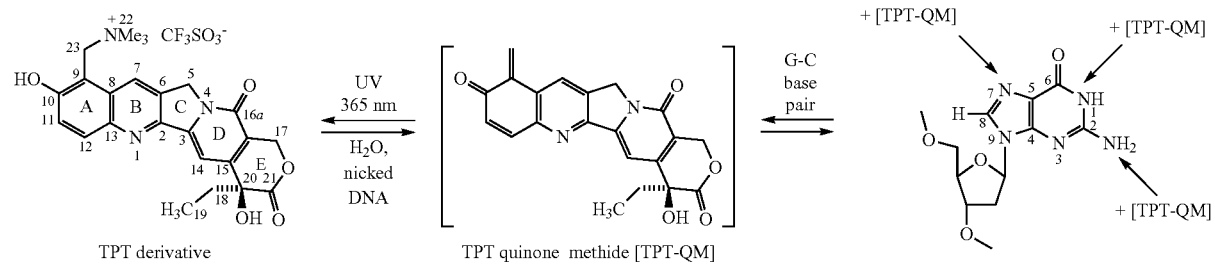

The next subject of the present invention is an intermediate compound (QM) o-methylenequinone defined by the formula (III) appropriate for substituting compounds defined by the formula (I) as defined above:

The progress of the reaction depends on the binding of TPT to the last GC base pair, as was shown in the case of the natural oligomer d(GCGATCGC)$_2$, inside the decomposition site in the DNA decamer.

The present invention is based on camptothecin derivatives and their synthesis, which makes it possible to obtain soluble derivatives with particularly preferable characteristics. Compounds according to the present invention make it possible to conduct an alkylation reaction of the nucleophilic nitrogen atom in bases being a part of tumour DNA in an effective and easy way. It was shown that compounds according to the present invention exhibit spontaneous or UV-induced binding with a DNA oligomer.

The subject of the present invention in its example embodiments is shown in the figures in which.

Figure 1:
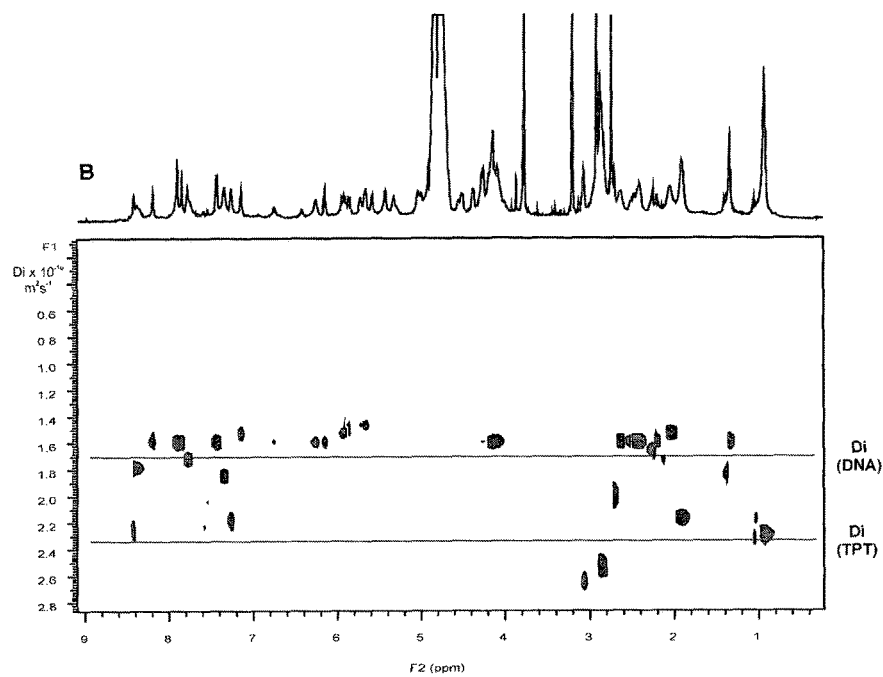
FIG. 1 represents PFGSE NMR analysis results for derivatives of DNA/TPT prior to UV exposure. The denoted lines indicate diffusion coefficients, Di, for DNA (with a non-covalently bound derivative of TPT), ca. $1.7 \times 10^{-10}$ m$^2$/s, and unbound derivative of TPT in a rapid exchange with DNA, $2.3 \times 10^{-10}$ m$^2$/s.

Due to the present invention, it was possible to obtain a covalent, spontaneous or UV-induced, DNA alkylation reaction by derivatives of camptothecin, as was shown in the following example embodiments using DNA oligomers.

The results obtained are very significant in terms of the use of the compounds according to the present invention in medicine, in particular in anti-cancer therapy.

In the embodiments of the present invention we give example compounds and prove the formation of conjugates using PFGSE NMR, which facilitates the easy differentiation of molecular complexes from covalent hybrid conjugates through a measurement of their diffusion coefficients. Moreover, the present invention was tested in biological systems using cancer lines, yielding a preferable IC$_{50}$ parameter value at a 20 µM concentration.

In light of the above, the present invention may constitute a breakthrough in chemotherapy due to the uncommonly preferable properties of the claimed compounds, thus delivering an effective tool for combating neoplastic diseases.

The present invention is disclosed using the following example embodiments, without limiting in any way the scope nor methods in which it may be embodied.

EXAMPLE I

Production of 7-ethyl-9-(N-morpholinyl)methyl-10-hydroxycamptothecin

SN38 (7-ethyl-10-hydroxycamptothecin) (3.3 mg; $8 \times 10^{-3}$ mmol) was suspended in 2.4 ml CH$_3$CN, and then supplemented with acetic acid (103 µL), 37% aqueous CH$_2$O (8 µL; 0.0986 mmol), 8.5 µl morpholine (0.098 mmol). The resulting mixture was mixed at a temperature of 80° C. After 10 h the solvent was evaporated off under a vacuum (at 40° C.) and rinsed with diethyl ether (3×1 mL). The resulting residue was lyophilized using 2 ml H$_2$O and dissolved in deuterated DMSO. On the basis of $^1$H NMR spectra, we detected the presence of two substances: SN38 and 7-ethyl-9-(N-morpholinyl)methyl-10-hydroxycamptothecin (efficiency: 33%). LR-MS (ESI): m/z 393 [M+H]$^+$, 492 [M+H]$^+$. The deuterated DMSO was evaporated off under a vacuum. The residue was extracted using 0.5% HCl (3×1 ml) in order to extract water-soluble derivatives of morpholinylcamptothecin. The insoluble 7-ethyl-10-hydroxycamptothecin was removed through filtration. Next, this was purified using HPLC on an RP-C18 LPH column (150 mm×10 mm) using the following liquid phase system: 20% CH$_3$CN/80% aqueous 0.1% HCOOH at a flow rate of 3 ml/min. The course of the chromatography was monitored using UV detection at a wavelength of 260 nm. Fractions were collected (retention time: 8.5 min) and were lyophilized yielding a pure product (>98%).

Spectral data: 7-ethyl-9-(N-morpholinyl)methyl-10-hydroxycamptothecin

LR-MS (ESI): m/z 492 [M+H]$^+$ $^1$H NMR δ (D$_2$O, TSPA) 500 MHz: 1.01 (t, J=7.3 Hz, 3H), 1.45 (t, J=7.3 Hz, 3H), 2.00 (m, 2H), 3.13 (m, 1H), 3.22 (m, 1H), 3.32 (m, 4H), 3.97 (m, 4H), 4.87 (d, J=15.0 Hz, 1H), 4.88 (d, J=15.0 Hz, 1H), 4.93 (d, J=18.7 Hz, 1H), 4.96 (d, J=18.7 Hz, 1H), 5.41 (J=16.14 Hz, 1H), 5.55 (J=16.14 Hz, 1H), 7.25 (d, J=9.17 Hz, 1H), 7.26 (s, 1H), 7.59 (d, J=9.17 Hz, 1H).

$^{13}$C NMR δ (D$_2$O, TSPA); HSQC 6.1, 13.4, 24.6, 30.5, 42.9, 49.8, 55.0. 63.4, 65.8, 97.8, 121.5, 130.7; HMBC 73.2, 117.5, 146.0. 146.9, 150.5, 174.30

UV nm: 378, 366, 329, 268, 224, 202.

IR (KBr) cm$^{-1}$:1038, 1056, 1108, 1162, 1261, 1303, 1383, 1423, 1463, 1513, 1593, 1656, 1744, 2853, 2922, 2958, 3401

EXAMPLE II

Production of 7-ethyl-9-(N-morpholinyl)methyl-10-hydroxycamptothecin

SN38 (2.9 mg, $7 \times 10^{-3}$ mmol) was suspended in 2.1 ml CH$_3$CN, and then supplemented with acetic acid (190 µL), 37% aqueous CH$_2$O (6.8 µL, 0.084 mmol), and morpholine (7.3 µL, 0.084 mmol). The resulting mixture was mixed at a temperature of 80° C. After 8 h was evaporated off under a vacuum soluble (w 40° C.) and rinsed with diethyl ether (3×1 ml). The resulting residue was lyophilized using 2 ml H$_2$O and dissolved in deuterated DMSO. On the basis of $^1$H NMR spectra, we noted the presence of two substances: SN38 and 7-ethyl-9-(N-morpholinyl)methyl-10-hydroxycamptothecin (efficiency: 25%). LR-MS (ESI): m/z 393 [M+H]$^+$, 492 [M+H]$^+$. The deuterated DMSO was evaporated off under a vacuum. The residue was extracted using 0.5% HCl (3×1 ml) in order to extract water-soluble derivatives of camptothecin. The insoluble camptothecin was removed through filtration. The purification of the residue was performed using HPLC in the following manner: the residue was dissolved in the liquid phase (20% CH$_3$CN, 80% 0.1% aqueous HCOOH) and loaded onto an RP-C18 LPH column 150 mm×10 mm, and then eluted at a rate of 3 ml/nm. The course of the chromatography was monitored using UV detection at 260 nm. Fractions were collected (retention time: 8.5 min) and were lyophilized yielding a pure product (>95%).

Spectral data: 7-ethyl-9-(N-morpholinyl)methyl-10-hydroxycamptothecin as in example I

EXAMPLE III

Production of 7-ethyl-9-(N-morpholinyl)methyl-10-hydroxycamptothecin

SN38 (2.27 mg, 5.54×10$^{-3}$ mmol) was suspended in 1.65 ml $CH_3CN$, and then supplemented with acetic acid (142 µl), 37% aqueous $CH_2O$ (10.8 µl; 0.133 mmol), morpholine (11.6 µl 0.133 mmol). The resulting mixture was mixed at a temperature of 80° C. After 6 h was evaporated off under a vacuum soluble (w 40° C.) and rinsed with diethyl ether (3×1 ml). The resulting residue was lyophilized using 2 ml $H_2O$ and dissolved in deuterated DMSO. On the basis of $^1H$ NMR spectra, we noted the presence of two substances: SN38 and 7-ethyl-9-N-morpholinylmethyl-10-hydroxycamptothecin (efficiency: 37%). LR-MS (ESI): m/z 393 $[M+H]^+$, 492 $[M+H]^+$. The deuterated DMSO was evaporated off under a vacuum. Residue was extracted using 0.5% HCl (3×1 ml) in order to extract water-soluble derivatives of camptothecin. The insoluble camptothecin was removed through filtration. The purification of the residue was performed using HPLC in the following manner: the residue was dissolved in the liquid phase (20% $CH_3CN$, 80% 0.1% aqueous HCOOH) and loaded onto a RP-C18 LPH column 150 mm×10 mm, and then eluted at a rate of 3 ml/min. The course of the chromatography was monitored using UV detection at 260 nm. Fractions were collected (retention time: 8.5 min) and were lyophilized yielding a pure product (>96%).

Spectral data: 7-ethyl-9-(N-morpholinyl)methyl-10-hydroxycamptothecin as in example I.

EXAMPLE IV

Alkylation of TPT[23]

Methyl trifluoromethanesulphonate (0.1 ml; 0.9 mmol) was dissolved in $CH_2Cl_2$ (3 ml), and then supplemented with a small quantity of $K_2CO_3$. The mixture was mixed for 30 min. in order to neutralize trifluoromethanesulphonic acid ($CF_3SO_3H$). The solution was filtered free of $K_2CO_3$, added to dry free TPT (1.8 mg; 4.4×10$^{-3}$ mmol) and was mixed for 24 h at room temperature. The mixture was evaporated off until dry under a vacuum at room temperature and dissolved in deuterated DMSO-d$_6$. On the basis of $^1H$ NMR spectra, we detected the presence of five products: N-methylated TPT-([$Me_3N^+CF_3SO_3^-$], TPT salt); N,O-dimethylated TPT, protonated TPT-[$TPTH^+CF_3SO_3^-$], and 23-$CH_2OH$ alcohol. N-methylated TPT ([$Me_3N^+CF_3SO_3^-$] salt TPT) constituted up to 50% of the mixture. We performed an LR ESI MS of the reaction mixture; LR-MS (ESI): m/z: 149 $[CF_3SO_3]^-$ 422 $[M+H]^+$, 436 $[M]^+$, 450 $[M]^+$.

The evaporated to dryness the reaction mixture was rinsed with water (5×1 ml). The precipitate was filtered off and the aqueous layer was lyophilized. Next, this was purified using HPLC on an RP-C18 LPH column (150 mm×10 mm) using the following liquid phases: 10% $CH_3CN$/90% aqueous 0.1% HCOOH for the first 15 min, whereafter the system was changed for 20% $CH_3CN$/80% aqueous 0.1% HCOOH with a steady flow rate of 3 ml/min. The course of the chromatography was monitored using UV detection at a wavelength of 260 nm. Fractions were collected (retention time: 25 min) and were lyophilized yielding 2 products.

LR-MS (ESI): m/z 422 $[M+H]^+$-[$TPTH^+CF_3SO_3$]-non-reactive in UV; 436 $[M]^+$[$Me_3N^+CF_3SO_3^-$] reactive UV.

Experimental Details of the HPLC

Chromatography in a reversed phase system, C-18, was performed using an analytical column (Bionacom Velocity C18 LPH, 4.6×250 mm, 5 microns) and a semi-preparative column (Bionacom Velocity C18 LPH, 10 mm×150 mm, 5 microns) in a Shimadzu LC-8A HPLC apparatus equipped with a Shimadzu SPD-6A UV spectrophotometric detector.

ESI MS Experimental Data

Solvent: 0.1% HCOOH, ACN 1:1; ion source: ESI; injected volume 1 µL; m/z range: 150-1500; ion retention time in the ion trap: 10 ms; detector voltage: 1.7 kV; interface voltage: 4.5 and −4.5 kV; CDL temperature: 200 C; Heat Block temperature: 200 C; carrier gas: 1.5 L/min; flow rate: 0.1 ml/min; wavelength: Ch1: 254 nm, Ch2: 220 nm; Apparatus: Shimadzu LCMS-IT-TOF.

EXAMPLE V

NMR Experiments Using Diffusion

Figure 2:
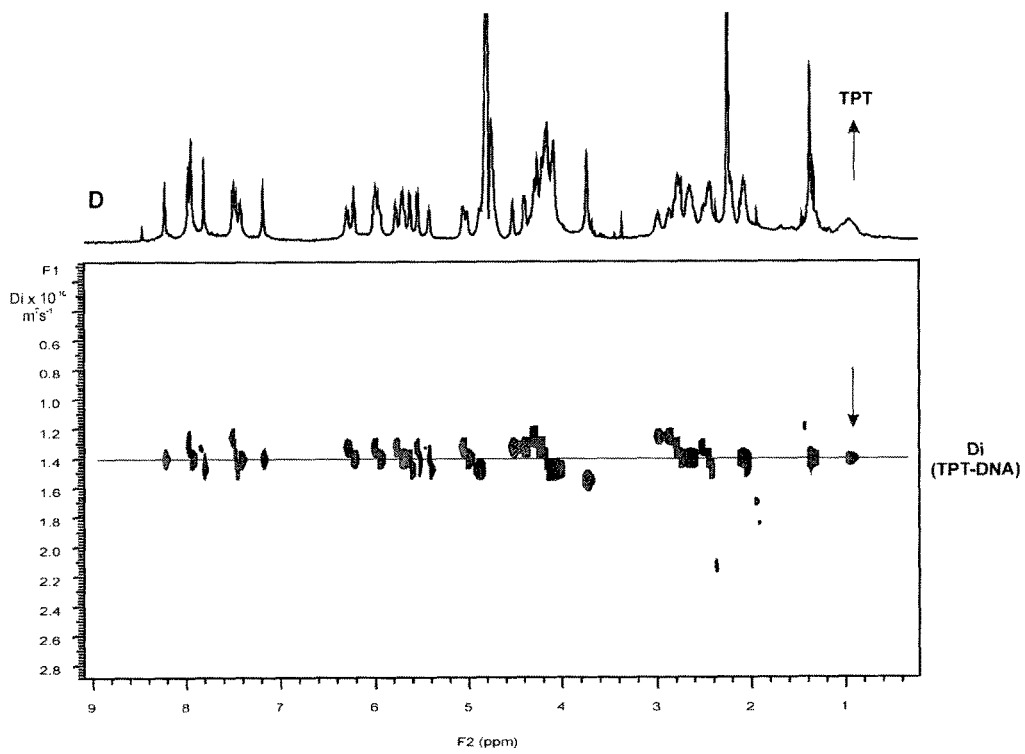
FIG. 2 represents a PFGSE NMR experiment using derivatives of DNA/TPT following UV exposure. The denoted lines indicate diffusion coefficients, Di, ca. $1.4 \times 10^{-10}$ m$^2$/s for the DNA-TPT bioconjugate.

We performed a PFGSE analysis using a DNA/TPT derivative prior to UV exposure (FIG. 1) and after UV exposure (FIG. 2). Next, we separated the unbound TPT derivative and analyzed it chromatographically using HPLC.

Based on the resulting spectrum, we detected a clear difference between the molecular complex and bioconjugate. The experimental results constitute evidence of the existence of a covalent bond between the chemically modified CPT unit and a DNA oligomer.

EXAMPLE VI

Sample Preparation and MALDI-TOF-MS Analysis

A dry sample prepared according to the above procedure, containing up to 50% TPT salt [$Me_3N^-$ $CF_3SO_3^-$], was added in excess (2 eq.) to an aqueous solution containing 1 mmol of the oligonucleotide d(GCGATCGC)$_2$ without buffer, in quartz NMR tubes. The solution was exposed using a UV lamp with a wavelength of 365 nm, for 20 hrs. The formed precipitate was filtered off, and the solution was evaporated off until dry under reduced pressure. In order to perform MALDI, the solid was dissolved in deionised water. The mass spectrum for negative MALDI ions was recorded using a Voyager-Elite apparatus (PerSeptive Biosystems Inc., Framingham, Mass., USA), equipped with a nitrogen laser (337 nm) in linear mode with an accelerating voltage of 20 kV and delayed ion extraction.

A mixture of 50 mg/ml of a 3-hydroxypicolinic acid solution in 50% acetonitrile and 50 mg/ml of a diammonium hydrocitrate solution in deionised in water (8:1, vol/vol) was used as a template. One µL of the oligonucleotide solution in deionised water at a concentration of 0.01 OD/µL was mixed on a MALDI plate with one µL of template and left to air dry. The mass spectrum was obtained from at least 100 laser impulses and transformed using Data Explorer Ver. 4 software (Applied Biosystems, Foster City, Calif.). MALDI-TOF analysis made it possible to obtain an m/z mass with an accuracy higher than 0.1% (i.e. ±1 mass unit for [M−1]$^-$ of 1000).

Figure 3:
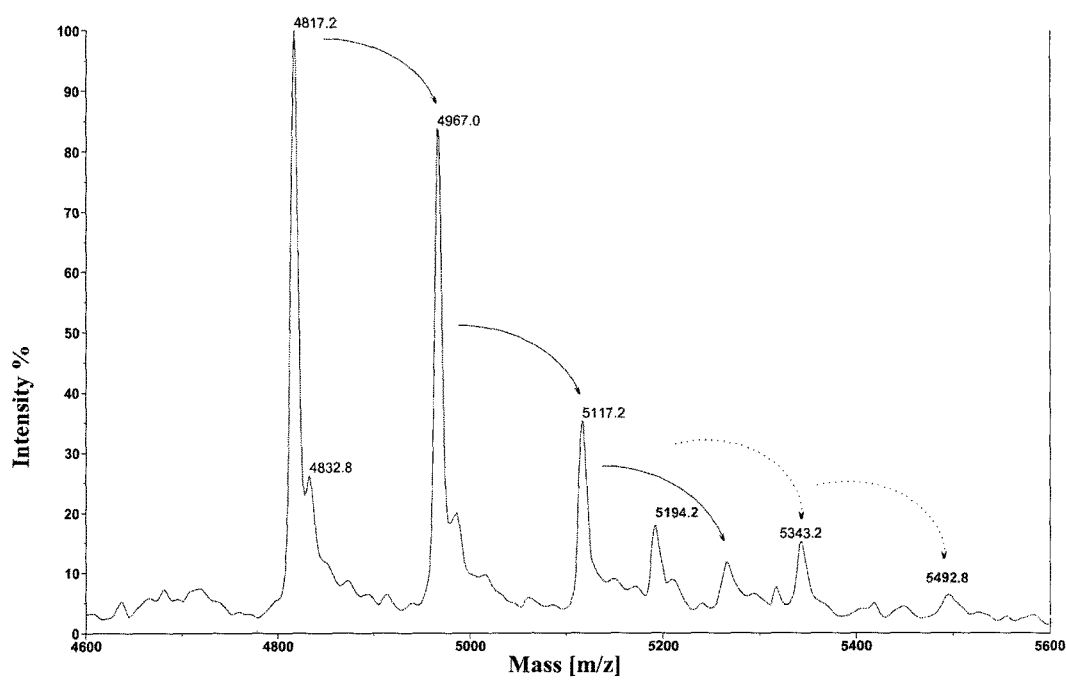
FIG. 3 represents a MALDI MS diagram for alkylation products of d(GCGATCGC)$_2$ using the salt [Me$_3$N$^+$ CF$_3$SO$_3^-$] TPT following UV exposure; the double-stranded (ds) region of the alkylated conjugate is shown alkylated. Solid arrows indicate unalkylated dsDNA, whereas dashed arrows indicate the monoalkyl conjugate of TPT.

MALDI MS analysis results for products of the d(GC-GATCGC)$_2$ alkylation using a TPT salt [$Me_3N^+CF_3SO_3^-$] following UV exposure show the existence of a double-stranded region in the alkylated conjugate of DNA, as shown in FIG. 3.

EXAMPLE VII

Biological Analysis of Cells
L1210 Murine Leukaemia Cell Line

The culture of L1210 murine leukaemia cells was conducted in RPMI-1640 medium, supplemented with 10% thermally inactivated foetal bovine serum, penicillin (100 UI/ml), streptomycin (100 µg/ml), amphotericin (250 ng/ml), L-glutamine (2 mM) and 1% non-essential aminoacids. The cells were cultured at 37° C., in an atmosphere of 5% $CO_2$ and 95% air. The medium was exchanged every 48 hours. For all experiments, the cells were inoculated at density of $1 \times 10^5$ cells/ml.

MTT Assay

This test is based on a measurement of the amount of formazan formed by the ability of mitochondrial dehydrogenase (part of the respiratory chain) to reduce the water-soluble 3-(4,5-dimethylthiazolo-2-ylo]-2,5-diphenyltetrazole (MTT) bromide. Damaged or dead cells exhibit a low or no dehydrogenase activity. This test may be used to determine cell viability. The solution of 7-ethyl-9-dimethylaminomethyl-10-hydroxycamptothecin or 7-ethyl-9-(N-morpholinyl)methyl-10-hydroxycamptothecin was prepared in DMSO. In order to determine the cytotoxicity of the evaluated compounds, L1210 cells were incubated for 24 hours with a solution of 7-ethyl-9-dimethylaminomethyl-10-hydroxycamptothecin or 7-ethyl-9-(N-morpholinyl)methyl-10-hydroxycamptothecin at concentrations of 1 µM, 5 µM, 10 µM, 20 µM, 30 µM, 40 µM and 50 µM. After centrifugation and rinsing with PBS buffer, the cells were incubated for 3 hours in MTT solution, and the crystals formed were dissolved using isopropanol. Formazan absorbance was measured on a "Power Wavex microplate" spectrophotometer (Biotek Instruments) at a wavelength of 570 nm.

Statistical Analysis

To evaluate the statistical significance of changes in the level of cytotoxicity we used analysis of variance (ANOVA) with Dunnett's post-hoc test at a significance level of $p<0.05$. Calculations were performed using the Statistica Ver. 9.0 package (StatSoft, Inc. USA).

MCF-7 Human Breast Cancer Line

The culture of the MCF-7 human breast cancer cell line was conducted in Eagle's Minimum Essential Medium (MEM), supplemented with 10% thermally inactivated foetal bovine serum, penicillin (100 UI/ml), streptomycin (100 µg/ml), amphotericin (250 ng/ml), L-glutamine (2 mM) and 1% non-essential aminoacids. The cells were cultured at 37° C., in an atmosphere of 5% $CO_2$ and 95% air. The medium was exchanged every 48 hours, and after 80% confluence was attained, the cells were passaged with a 0.25% trypsin solution. In all experiments, cells were inoculated at a density of $5 \times 10^4$ cells/ml.

Test MTT

This test is based on a measurement of the amount of formazan formed by the ability of mitochondrial dehydrogenase (part of the respiratory chain) to reduce the water-soluble 3-(4,5-dimethylthiazolo-2-ylo]-2,5-diphenyltetrazole (MTT) bromide. Damaged or dead cells exhibit a low or no dehydrogenase activity. This test may be used to determine cell viability. The solution of 7-ethyl-9-dimethylaminomethyl-10-hydroxycamptothecin or 7-ethyl-9-(N-morpholinyl)methyl-10-hydroxycamptothecin was prepared in DMSO. In order to determine the cytotoxicity of the evaluated compounds, cells MCF-7 were incubated for 24 hours with a solution of 7-ethyl-9-dimethylaminomethyl-10-hydroxycamptothecin or 7-ethyl-9-(N-morpholinyl)methyl-10-hydroxycamptothecin at concentrations of 1 µM, 5 µM, 10 µM, 20 µM, 30 µM, 40 µM and 50 µM. After rinsing with PBS buffer, cells were incubated for 3 hours in MTT solution, and the crystals formed were dissolved using isopropanol. Formazan absorbance was measured w "Power Wavex microplate" spectrophotometer (Biotek Instruments) at a wavelength of 570 nm.

Statistical Analysis

To evaluate the statistical significance of changes in the level of cytotoxicity we used analysis of variance (ANOVA) with Dunnett's post-hoc test at a significance level of $p<0.05$. Calculations were performed using the Statistica Ver. 9.0 package (StatSoft, Inc. USA).

Caco-2 Human Colon Cancer Line

The culture of Caco-2 human colon cancer cells was conducted in Eagle's Minimum Essential Medium Eagle (MEM), supplemented with 20% thermally inactivated foetal bovine serum, penicillin (100 UI/ml), streptomycin (100 µg/ml), amphotericin (250 ng/ml), L-glutamine (2 mM) and 1% non-essential amine. The cells were cultured at 37° C., in an atmosphere of 5% $CO_2$ and 95% air. The medium was exchanged every 48 hours, and after 80% confluence was attained, the cells were passaged with a 0.25% trypsin solution. In all experiments, cells were inoculated at a density of $6.5 \times 10^4$ cells/ml.

Test MTT

This test is based on a measurement of the amount of formazan formed by the ability of mitochondrial dehydrogenase (part of the respiratory chain) to reduce the water-soluble 3-(4,5-dimethylthiazolo-2-ylo]-2,5-diphenyltetrazole (MTT) bromide. Damaged or dead cells exhibit a low or no dehydrogenase activity. This test may be used to determine cell viability. The solution 7-ethyl-9-dimethylaminomethyl-10-hydroxycamptothecin or 7-ethyl-9-(N-morpholinyl)methyl-10-hydroxycamptothecin was prepared in DMSO. In order to determine the cytotoxicity of the evaluated compounds, cells Caco-2 were incubated for 24 hours with a solution of 7-ethyl-9-dimethylaminomethyl-10-hydroxycamptothecin or 7-ethyl-9-(N-morpholinyl)methyl-10-hydroxycamptothecin at concentrations of 1 µM, 5 µM, 10 µM, 20 µM, 30 µM, 40 µM and 50 µM. After rinsing with PBS buffer cells were incubated for 3 hours in MTT solution and the crystals formed were dissolved using isopropanol. Formazan absorbance was measured in "Power Wavex" microplate spectrophotometer (Biotek Instruments) at a wavelength of 570 nm.

Statistical Analysis

To evaluate the statistical significance of changes in the level of cytotoxicity we used analysis of variance (ANOVA) with Dunnett's post-hoc test at a significance level of $p<0.05$. Calculations were performed using the Statistica Ver. 9.0 package (StatSoft, Inc. USA).

Figure 4:
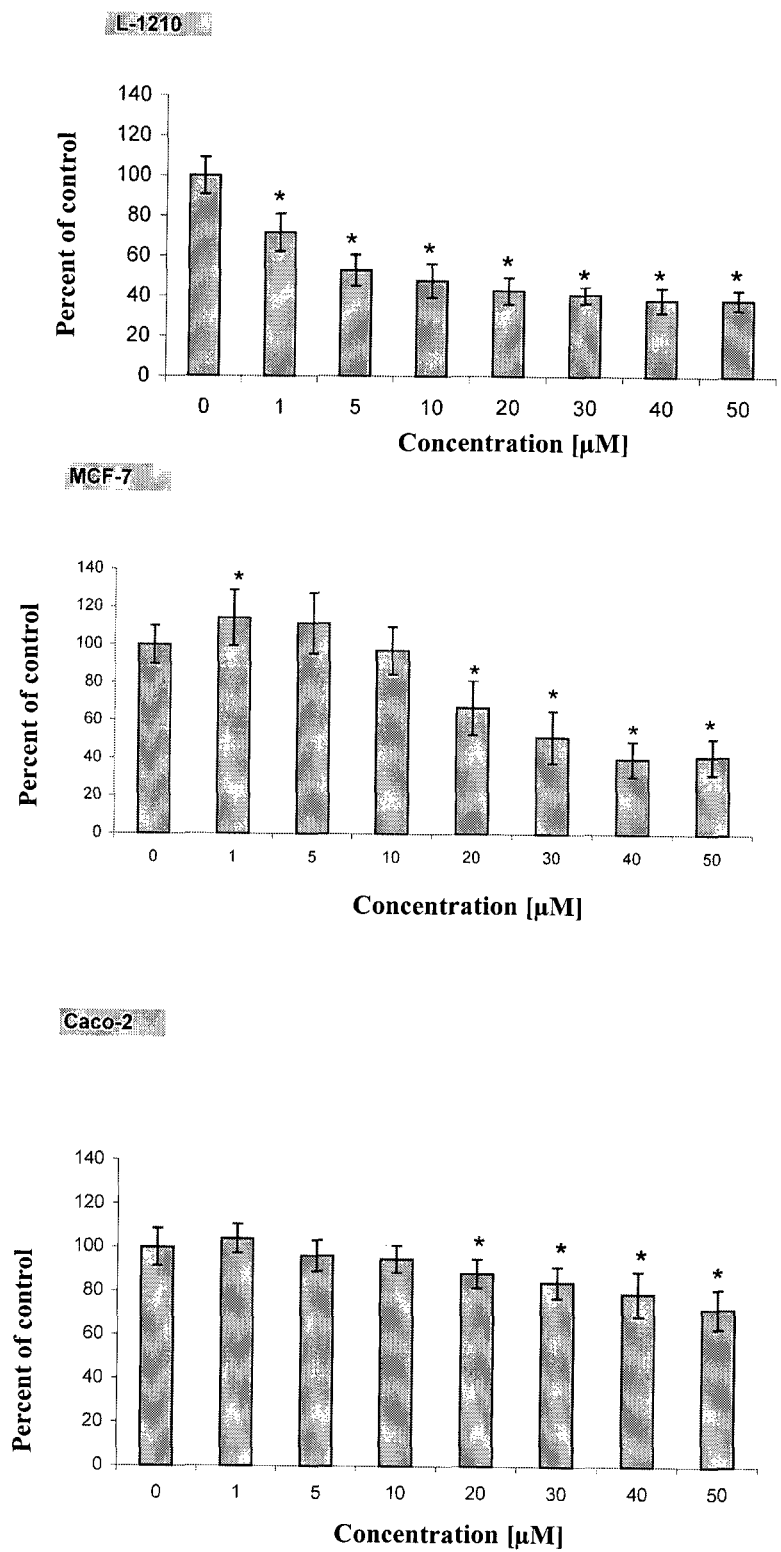
FIG. 4 represents biological analysis results using 7-ethyl-9-dimethylaminomethyl-10-hydroxycamptothecin with three evaluated cell lines: L-1210-murine leukaemia, MCF-7—human breast cancer cells and Caco-2 (human colon cancer cells)
Figure 5:
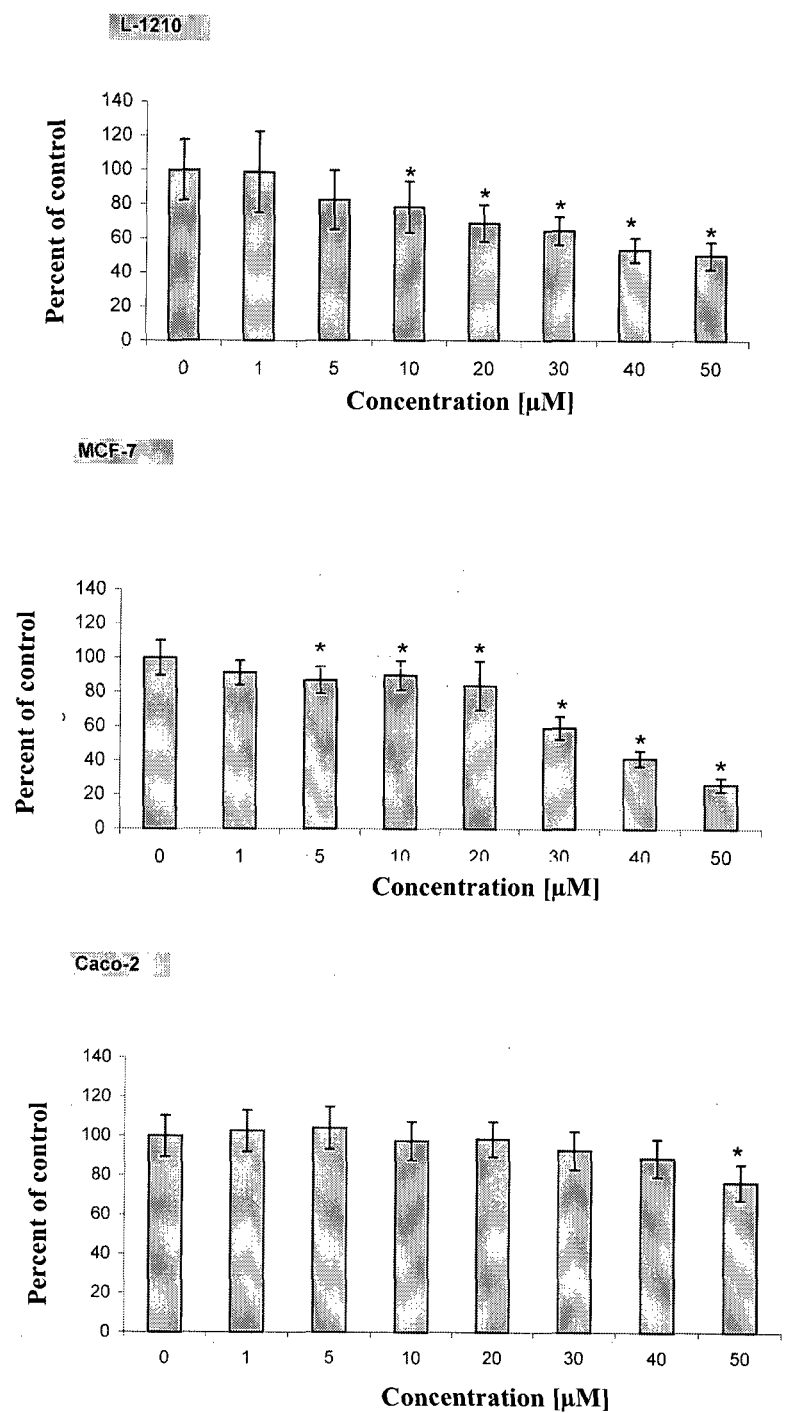
FIG. 5 represents biological analysis results using 7-ethyl-9-(N-morpholinyl)methyl-10-hydroxycamptothecin with three evaluated cell lines: L-1210-murine leukaemia, MCF-7—human breast cancer cells and Caco-2 (human colon cancer cells)
Figure 6:
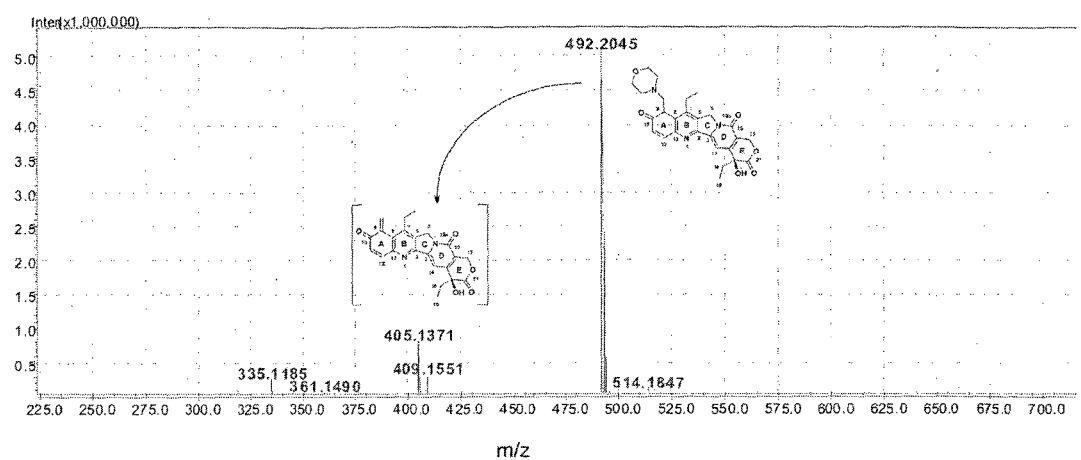
FIG. 6 represents the ESI MS spectrum of the compound defined in claim 1 with a visible o-methylenequinone signal, m/z 405.1371.

The biological analysis results using 7-ethyl-9-dimethylaminomethyl-10-hydroxycamptothecin in the three evaluated cell lines: L-1210-murine leukaemia cells, MCF-7-human breast cancer cells and Caco-2 human colon cancer cells are shown in FIG. 4. The biological analysis results using 7-ethyl-9-(N-morpholinyl)methyl-10-hydroxycamptothecin in the three evaluated cell lines: L-1210-murine leukaemia cells, MCF-7-human breast cancer cells and Caco-2 human colon cancer cells are shown in FIG. 5.

EXAMPLE VIII

Title: Materials and Experimental Methods Used
Experimental Details

DNA oligomers were purchased from Integrated DNA Technologies, Inc. and purified as described.[12] The oligonucleotide d(GCGATCGC)$_2$ from Integrated DNA Technologies, Inc. was purified using ion exchange chromatography, using a HiTrap™-Q column (Pharmacia Biotech) using gradient elution with ammonium bicarbonate (0.1 M-0.8 M) and desalted on a column packed with Sephadex G-10. Purity>95+

Topotecan hydrochloride was purchased from Alexis Biochemicals and used directly without additional purification. Purity>98+

In order to obtain the free TPT base, topotecan hydrochloride (2 mg, 4.4×10$^{-3}$ mmol) was dissolved in H$_2$O (0.5 mL) and pH was set to 7 using aqueous NaHCO$_3$. Free TPT was extracted using CH$_2$Cl$_2$ and dried under a vacuum.

Sample Preparation $^1$H NMR spectra were obtained using a VARIAN VNMRS 500 MHz spectrometer using a Nalorac ID probe equipped with a gradient unit generating a gradient of 60 Gs/cm along the Z axis, at a temperature of 25.0° C. Chemical shifts were made in reference to TSPA as an internal standard dissolved in D$_2$O.

The parameters of the $^1$H NMR analysis were: 25.3° C.; sw=8000 Hz (spectrum range); nt=16, or 64, or 256; (number of scans), 32 K memory points; at=2 s (acquisition time), d1=6 s (relaxation delay), satdly=2 s (presaturation delay), 1b=0.3 Hz (line broadening).

Analysis parameters $^{13}$C NMR; 25.0° C.;

The $^1$H/$^{13}$C-HSQC. $^1$H-$^{13}$C HSQC spectra (heteronuclear single quantum correlation) were obtained using a spectrum range of 5000 Hz, 2048 points in the $^1$H domain and 8000 Hz, 800×2 increments in the $^{13}$C domain; 128 scans per increment $t_1$, with a relaxation delay of 1 s and $^1$J(C,H)=135 Hz. The data were linearly extrapolated to 1600 points and filled with zeros to 4096 points in F$_1$ prior to a Fourier transformation.

$^1$H/$^{13}$C-HMBC spectra (heteronuclear multiple bonds correlation) HMBC spectra with a gradient coherence of $^1$H-$^{13}$C were obtained, using an acquisition time of 0.2 s, $^1$H-90° impulse width of 7.8 μs, $^{13}$C-90° impulse width of 11.5 μs, spectrum range of 5000 Hz, 2048 given points in the $^1$H dimension and 25000 Hz, 1024 increments in the $^{13}$C dimension, and a relaxation delay of 1.2 s. Data were obtained in the form of absolute values, using 64 scans per $t_1$ increment. The experiment was optimized for $^n$J(C,H)=8 Hz, and for $^1$J(C,H)=140 Hz with a low-pass filter. The data were linearly extrapolated to 2048 points and filled with zeros to 4096 points in F$_1$ prior to a Fourier transformation. (PFGSE) (Pulsed Field Gradient Spin Echo) (Diffusion Measurement Experiments)

DOSY NMR is a method with a high potential for analysing mixtures of chemical compounds in solution, used to measure the translation coefficient of diffusion $D_t$. Larger molecules diffuse much slower than smaller ones. Each spectral line in the $^1$H-1D NMR spectrum of a given chemical individual is characterised in terms of the same $D_t$ coefficient, differing for each molecule with a different molecular mass.

The experiments were performed using the following conditions: 16 spectra were collected using the PFGDSTE sequence[18] (Double Stimulated Echo with convection compensation) with an initial saturation of the residual water signal. The gradient coil value was calibrated using the known water diffusion coefficient ($D_t$=19.02×10$^{-10}$ m$^2$/s)[19]. The gradient strength was increased as a square function in the range from 2 to 50 G/cm. The diffusion time (Δ) and duration of the magnetic field gradient (δ) were 150 ms and 1.0 ms, respectively. The remaining parameters were: sweep width of 8000 Hz, 32K memory points, 64 scans and a data acquisition time of 2.7 s and a relaxation delay of 2 s and 16 dummy scans. Data are transformed using a Varian package for DOSY[17].

LITERATURE

1. Wang, J. C. DNA topoisomerases. *Annu. Rev. Biochem.* 1996, 65, 635-92.
2. Stewart, L.; Redinbo, M. R.; Qiu, X.; Hol, W. G.; Champoux, J. J. A model for the mechanism of human topoisomerase I. *Science* 1998, 279, 1534-41.
3. Redinbo, M. R.; Stewart, L.; Kuhn, P.; Champoux, J. J.; Hol, W. G. J. Crystal structures of human topoisomerase I in covalent and noncovalent complexes with DNA. *Science* 1998, 279, 1504-1513.
4. Pizzolato, J. F.; Saltz, L. B. The camptothecins. *Lancet* 2003, 361, 2235-42.
5. Zunino, F.; Pratesi, G. Camptothecins in clinical development. *Expert Opin. Investig. Drugs* 2004, 13, 269-84.
6. Takimoto, C. H.; Wright, J.; Arbuck, S. G. Clinical applications of the camptothecins. *Biochim. Biophys. Acta* 1998, 1400. 107-19.
7. Rivory, L. P.; Robert, J. Pharmacology of camptothecin and its derivatives. *Bull. Cancer* 1995, 82, 265-285.
8. Slichenmyer, W. J.; Rowinsky, E. K.; Donehower, R. C.; Kaufmann, S. H. The current status of camptothecin analogs as antitumor agents. *J. Natl. Cancer Inst.* 1993, 85, 271-291.
9. Staker, B. L.; Hjerrild, K.; Feese, M. D.; Behnke, C. A.; Burgin, A. B.; Stewart, L. The mechanism of topoisomerase I poisoning by a camptothecin analog. *Proc. Natl. Acad. Sci. USA* 2002, 99, 15387-15392.
10. Pommier, Y.; Kohlhagen, G.; Kohn, K. W.; Leteurtre, F.; Wani, M. C.; Wall, M. E. Interaction of an alkylating camptothecin derivative with a DNA base at topoisomerase I-DNA cleavage sites. *Proc. Natl. Acad. Sci. USA* 1995, 92, 8861-8865.
11. Dallavalle, S., Merlini, L. Camptothecin and Analogs: Structure and Synthetic Efforts. In *Modern Alkaloids*, Prof Ernesto Fattorusso, P. O. T.-S., Ed. 2007; pp 503-520.
12. Bocian, W.; Kawecki, R.; Bednarek, E.; Sitkowski, J.; Williamson, M. P.; Hansen, P. E.; Kozerski, L. Binding of Topotecan to a Nicked DNA Oligomer in Solution. *Chem. Eur. J.* 2008, 14, 2788-2794.
13. Reedijk, J. Why does Cisplatin reach Guanine-n7 with competing s-donor ligands available in the cell? *Chem. Rev.* 1999, 99, 2499-510.
14. Pande, P.; Shearer, J.; Yang, J.; Greenberg, W. A.; Rokita, S. E. Alkylation of Nucleic Acids by a Model Quinone Methide. *J. Am. Chem. Soc.* 1999, 121, 6773-6779.
15. Veldhuyzen, W. F.; Lam, Y. F.; Rokita, S. E. 2'-Deoxyguanosine reacts with a model quinone methide at multiple sites. *Chem. Res. Toxicol.* 2001, 14, 1345-51.
16. Svoboda, J.; Konig, B. Templated photochemistry: toward catalysts enhancing the efficiency and selectivity of photoreactions in homogeneous solutions. *Chem. Rev.* 2006, 106, 5413-30.
17. Johnson, C. S. Diffusion Ordered NMR Spectroscopy: Principles and Applications. *Prog. Nucl. Magn. Reson.* 1999, 34, 203-255.

18. Nilsson, M.; Gil, A. M.; Delgadillo, I.; Morris, G. A. Improving pulse sequences for 3D diffusion-ordered NMR spectroscopy: 2DJ-IDOSY. *Anal Chem.* 2004, 76, 5418-22.
19. Mills, R. Self-Diffusion in Normal and Heavy Water in the Range 1-45 C. *J. Phys. Chem.* 1973, 77, 685-688.

The invention claimed is:

1. A compound defined by the general formula (I)

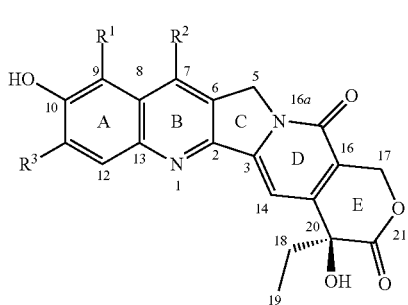

where $R^1$ denotes (N-piperidinyl)methyl, (N-piperazinyl)methyl, (N—(N-methylpiperazinyl)methyl, (N-morpholinyl)methyl, (N-pyrrolidinyl)methyl, (N-azetidinyl)methyl, (N-aziridinyl)methyl, (N-methylamino)methyl;

$R^2$ denotes ethyl;

$R^3$ denotes H, (N-piperidinyl)methyl, (N-piperazinyl)methyl, (N—(N-methylpiperazinyl)methyl, (N-morpholinyl)methyl, (N-pyrrolidinyl)methyl, (N-azetidinyl)methyl, (N-aziridinyl)methyl, (N-methylamino)methyl.

2. A method of obtaining the compound defined in claim 1, comprising reacting 7-ethyl-10-hydroxycamptothecin with an amine and formaldehyde in an environment of acetonitrile and acetic acid at boiling temperature,
wherein the amine is piperidine, piperazine, N-methylpiperazine, morpholine, pyrrolidine, azetidine, aziridine, methylamine, or diethylamine.

3. A compound selected from a group consisting of:
7-ethyl-9-(N-morpholinyl)methyl-10-hydroxycamptothecin,
7-ethyl-11-(N-morpholinyl)methyl-10-hydroxycamptothecin,
7-ethyl-9,11-bis(N-morpholinyl)methyl-10-hydroxycamptothecin,
7-ethyl-9-(N-piperidinyl)methyl-10-hydroxycamptothecin,
7-ethyl-11-(N-piperidinyl)methyl-10-hydroxycamptothecin,
7-ethyl-9,11-bis(N-piperidinyl)methyl-10-hydroxycamptothecin,
7-ethyl-9-(N-piperazinyl)methyl-10-hydroxycamptothecin,
7-ethyl-11-(N-piperazinyl)methyl-10-hydroxycamptothecin,
7-ethyl-9,11-bis(N-piperazinyl)methyl-10-hydroxycamptothecin,
7-ethyl-9-(N—(N-methylpiperazinyl)methyl-10-hydroxycamptothecin,
7-ethyl-11-(N—(N-methylpiperazinyl)methyl-10-hydroxycamptothecin,
7-ethyl-9,11-bis(N—(N-methylpiperazinyl)methyl-10-hydroxycamptothecin,
7-ethyl-9-(N-pyrrolidinyl)methyl-10-hydroxycamptothecin,
7-ethyl-11-(N-pyrrolidinyl)methyl-10-hydroxycamptothecin,
7-ethyl-9,11-bis(N-pyrrolidinyl)methyl-10-hydroxycamptothecin,
7-ethyl-9-(N-azetidinyl)methyl-10-hydroxycamptothecin,
7-ethyl-11-(N-azetidinyl)methyl-10-hydroxycamptothecin,
7-ethyl-9,11-bis(N-azetidinyl)methyl-10-hydroxycamptothecin,
7-ethyl-9-(N-aziridinyl)methyl-10-hydroxycamptothecin,
7-ethyl-11-(N-aziridinyl)methyl-10-hydroxycamptothecin,
7-ethyl-9,11-bis(N-aziridinyl)methyl-10-hydroxycamptothecin,
7-ethyl-9-(N-methylamino)methyl-10-hydroxycamptothecin,
7-ethyl-11-(N-methylamino)methyl-10-hydroxycamptothecin,
7-ethyl-9,11-bis(N-methylamino)methyl-10-hydroxycamptothecin,
7-ethyl-11-(N,N-diethylamino)methyl-10-hydroxycamptothecin,
7-ethyl-9,11-bis(N,N-diethylamino)methyl-10-hydroxycamptothecin.

4. An intermediate compound (-QM) o-methylenequinone defined by the formula (II):

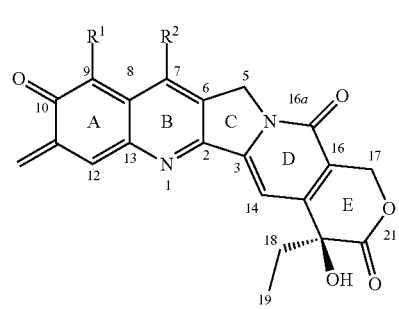

where $R^1$ denotes (N-piperidinyl)methyl, (N-piperazinyl)methyl, (N—(N-methylpiperazinyl)methyl, (N-morpholinyl)methyl, (N-pyrrolidinyl)methyl, (N-azetidinyl)methyl, (N-aziridinyl)methyl, (N-methylamino)methyl, (N,N-diethylamino)methyl;

$R^2$ denotes ethyl;

or $R^1$ denotes H; $R^2$ denotes ethyl.

5. An intermediate compound (-QM) o-methylenequinone defined by the formula (III):

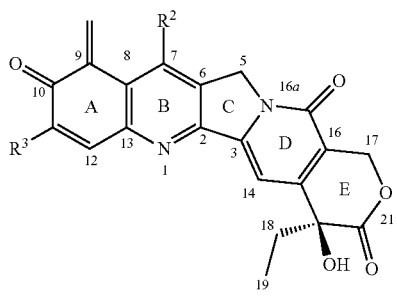

where R² denotes ethyl; R³ denotes H, (N-piperidinyl)methyl, (N-piperazinyl)methyl, (N—(N-methylpiperazinyl)methyl, (N-morpholinyl)methyl, (N-pyrrolidinyl)methyl, (N-azetidinyl)methyl, (N-aziridinyl)methyl, (N-methylamino)methyl, (N,N-diethylamino)methyl;

or R² denotes ethyl; R³ denotes (N-piperidinyl)methyl, (N-piperazinyl)methyl, (N—(N-methylpiperazinyl)methyl, (N-morpholinyl)methyl, (N-pyrrolidinyl)methyl, (N-azetidinyl)methyl, (N-aziridinyl)methyl, (N-methylamino)methyl, (N,N-diethylamino)methyl.

6. A pharmaceutical composition comprising the compound of claim 1 and a pharmaceutical carrier.

7. A pharmaceutical composition comprising the compound of claim 3 and a pharmaceutical carrier.

8. A method of treating breast cancer, leukemia or colon cancer in a subject comprising administering to the subject the compound of claim 1.

9. A method of treating breast cancer, leukemia or colon cancer in a subject comprising administering to the subject the compound of claim 3.

10. The compound according to claim 3, characterised in that it is a compound selected from a group consisting of:
    7-ethyl-9-(N-morpholinyl)methyl-10-hydroxycamptothecin,
    7-ethyl-9,11-bis(N-morpholinyl)methyl-10-hydroxycamptothecin,
    7-ethyl-9-(N-piperidinyl)methyl-10-hydroxycamptothecin,
    7-ethyl-9,11-bis(N-piperidinyl)methyl-10-hydroxycamptothecin,
    7-ethyl-9-(N-piperazinyl)methyl-10-hydroxycamptothecin,
    7-ethyl-9,11-bis(N-piperazinyl)methyl-10-hydroxycamptothecin,
    7-ethyl-9-(N—(N-methylpiperazinyl)methyl-10-hydroxycamptothecin,
    7-ethyl-9,11-bis(N—(N-methylpiperazinyl)methyl-10-hydroxycamptothecin,
    7-ethyl-9-(N-pyrrolidinyl)methyl-10-hydroxycamptothecin,
    7-ethyl-9,11-bis(N-pyrrolidinyl)methyl-10-hydroxycamptothecin,
    7-ethyl-9-(N-azetidinyl)methyl-10-hydroxycamptothecin,
    7-ethyl-9,11-bis(N-azetidinyl)methyl-10-hydroxycamptothecin,
    7-ethyl-9-(N-aziridinyl)methyl-10-hydroxycamptothecin,
    7-ethyl-9,11-bis(N-aziridinyl)methyl-10-hydroxycamptothecin,
    7-ethyl-9-(N-methylamino)methyl-10-hydroxycamptothecin,
    7-ethyl-9,11-bis(N-methylamino)methyl-10-hydroxycamptothecin.

11. An intermediate compound (-QM) o-methylenequinone defined by the formula (II):

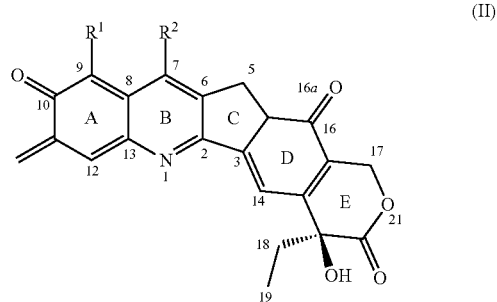

(II)

where R¹ denotes (N-piperidinyl)methyl, (N-piperazinyl)methyl, (N—(N-methylpiperazinyl)methyl, (N-morpholinyl)methyl, (N-pyrrolidinyl)methyl, (N-azetidinyl)methyl, (N-aziridinyl)methyl, (N-methylamino)methyl; R² denotes ethyl; or R¹ denotes H; R² denotes ethyl.

* * * * *